United States Patent
Kim et al.

(10) Patent No.: US 10,403,360 B2
(45) Date of Patent: Sep. 3, 2019

(54) NONVOLATILE PROTEIN MEMORY SYSTEM WITH OPTICAL WRITE/ERASE AND ELECTRICAL READOUT CAPABILITY

(71) Applicants: Konkuk University Industrial Cooperation Corp, Seoul (KR); Myongji University Industry and Academia Cooperation Foundation, Yongin-si (KR); Hongik University Industry-Academia Cooperation Foundation, Seoul (KR)

(72) Inventors: Dohyun Kim, Yongin-si (KR); Jin Song, Yongin-si (KR); Jintae Kim, Seoul (KR); Minsub Chung, Seoul (KR); Kyungju Song, Seoul (KR); Yeji Kim, Seoul (KR)

(73) Assignees: KONKUK UNIVERSITY INDUSTRIAL COOPERATION CORP, Seoul (KR); MYONGJI UNIVERSITY INDUSTRY AND ACADEMIA COOPERATION FOUNDATION, Gyeonggi-Do (KR); HONGIK UNIVERSITY INDUSTRY-ACADEMIA COOPERATION FOUNDATION, Seoul (KR)

( * ) Notice: Subject to any disclaimer, the term of this patent is extended or adjusted under 35 U.S.C. 154(b) by 0 days.

(21) Appl. No.: 15/994,630

(22) Filed: May 31, 2018

(65) Prior Publication Data
US 2018/0350436 A1    Dec. 6, 2018

(30) Foreign Application Priority Data
May 31, 2017    (KR) .................. 10-2017-0067881

(51) Int. Cl.
G11C 13/04 (2006.01)
G01N 27/02 (2006.01)

(52) U.S. Cl.
CPC ......... *G11C 13/048* (2013.01); *G01N 27/028* (2013.01)

(58) Field of Classification Search
None
See application file for complete search history.

(56) References Cited

U.S. PATENT DOCUMENTS 6,005,791 A * 12/1999 Gudesen .............. B82Y 10/00
                                                365/114

OTHER PUBLICATIONS

Britta Walowski et al., "Generation of a miniaturized free-flow electrophoresis chip based on a multi-lamination technique—isoelectric focusing of proteins and a single-stranded DNA fragment", Anal Bioanal Chem, (2011), vol. 401, pp. 2465-2471.

* cited by examiner

*Primary Examiner* — James G Norman
(74) *Attorney, Agent, or Firm* — Cantor Colburn LLP

(57) ABSTRACT

A nonvolatile protein memory system with optical write/erase and electrical readout capability is provided. The nonvolatile protein memory system includes: a substrate including a microfluidic channel having a pH gradient; a photosensitive protein disposed in the microfluidic channel; and a first electrode and a second electrode disposed on the microfluidic channel and spaced apart from each other and detecting a position change of the photosensitive protein in the microfluidic channel.

18 Claims, 7 Drawing Sheets
(2 of 7 Drawing Sheet(s) Filed in Color)

Read

[FIG. 6]

Erase

NONVOLATILE PROTEIN MEMORY SYSTEM WITH OPTICAL WRITE/ERASE AND ELECTRICAL READOUT CAPABILITY

CROSS-REFERENCE TO RELATED APPLICATION

This application claims priority to and the benefit of Korean Patent Application No. 10-2017-0067881 filed in the Korean Intellectual Property Office on May 31, 2017, the entire contents of which are incorporated herein by reference.

BACKGROUND OF THE INVENTION

(a) Field of the Invention

This disclosure relates to a nonvolatile protein memory system. More particularly, the present invention relates to a nonvolatile protein memory system with optical write/erase and electrical readout capability.

(b) Description of the Related Art

Bioelectronics in which merits of a semiconductor device are combined with merits of biometric materials is drawing attention as a technique for compensating the conventional silicone-based semiconductor due to a fast information transmission capability, high energy efficiency, a high-density integration capability, low heat generation, a capability of multiplexed information processing, and a bio-compatibility.

However, the conventional bioelectronic devices have fundamental problems as follows: (1) a bottom-up process by self-assembly is limited; (2) interfacing with an external device is difficult; and (3) down-sizing is difficult (for an optics-based memory device).

A memory device using a photochromic protein using bacteriorhodopsin carries out optical write, erase, and readout operations, but a size of the additional optical system and complexity thereof limit its commercialization.

A memory device using a photoswitching property of a genetically modified fluorescent protein of rsEGFP also has a demerit of using a complex optical system, and still remains in an idea verification stage.

In a case of microfluidic LSI using a pneumatic-based microscale PDMS valve and pump network which was suggested by the Quake group of Stanford University, it has problems in that the pneumatic system is complicated and a switching speed is slow.

In Korea, a memory device based on a change of oxidation/reduction of an azurin copper protein fixed in a gold electrode has been developed. However, the memory device has demerits of leaking a charge stored in the protein and of continuously refreshing the memory state due to the continuous charge leakage even in a readout operation.

SUMMARY OF THE INVENTION

This disclosure provides a nonvolatile protein memory system which is easily designed.

This disclosure provides a nonvolatile protein memory system which may maintain a memory state during a readout operation as the memory state is maintained in the readout operation.

This disclosure provides a nonvolatile protein memory system which is capable of being simplified and down-sized.

This disclosure also provides a nonvolatile protein memory system which is biocompatible so as to be employed for a biological system such as human or animal.

An embodiment of the present invention may be employed for achieving other objects besides the objects specifically mentioned above.

A nonvolatile protein memory system according to one embodiment includes at least one memory cell, wherein the memory cell includes: a substrate including a microfluidic channel having a pH gradient; a photosensitive protein disposed in the microfluidic channel; and a first electrode and a second electrode disposed on the microfluidic channel, spaced apart from each other, and detecting a position change of the photosensitive protein in the microfluidic channel.

A nonvolatile protein memory system according to another embodiment includes: a memory cell including a substrate including a microfluidic channel having a pH gradient, a photosensitive protein disposed in the microfluidic channel, and a first electrode and a second electrode disposed on the microfluidic channel and spaced apart from each other and detecting a position change of the photosensitive protein in the microfluidic channel; a light source causing a position change of the photosensitive protein; and a readout circuit measuring impedance between the first electrode and the second electrode in a non-contact manner.

It is easy to fabricate the nonvolatile protein memory system by employing a microfluidic MEMS fabrication technique using CAD, a foundry service, etc.

The write/erase are performed optically, while the readout is performed electrically, so the reading operation does not influence the state of the memory cell. Thus it is possible to perform continuous write and erase without an additional operation such as a refresh.

As the electrical readout is operated by measuring conductivity in a non-contact manner based on a CMOS integrated circuit technique, it is possible to reduce power of the system and to down-size the same, such that it may be integrated with a wearable device or a smart device. It is applicable for a bio-implant by using a biocompatible chip material, a protein, and an electrode material.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Hereinafter, the present invention will be described more fully with reference to the accompanying drawings, in which example embodiments of the invention are shown.

As those skilled in the art would realize, the described embodiments may be modified in various different ways, all without departing from the spirit or scope of the present invention. Parts that are irrelevant to the description will be omitted to clearly describe the present invention, and the same or similar constituent elements will be designated by the same reference numerals throughout the specification. In addition, detailed description of widely known technologies will be omitted.

In addition, unless explicitly described to the contrary, the word "comprise" and variations such as "comprises" or "comprising" will be understood to imply the inclusion of stated elements but not the exclusion of any other elements.

Figure 1:
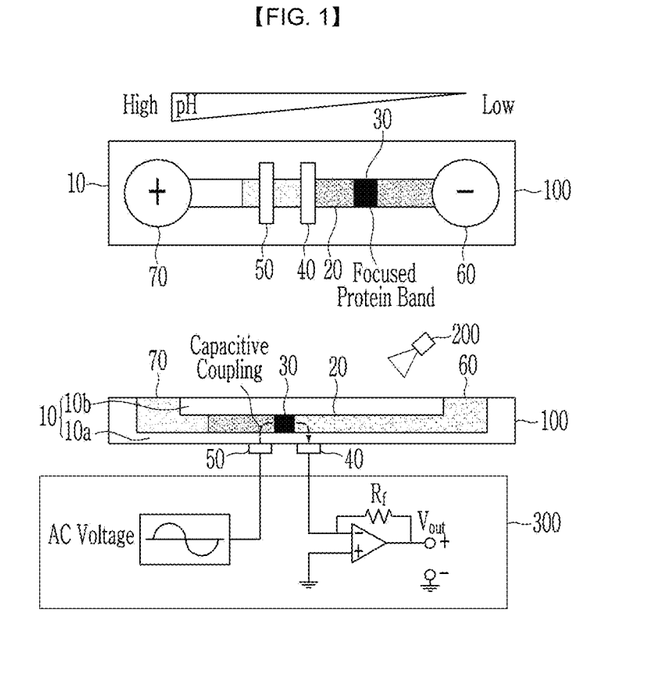
FIG. 1 shows a plane view and a cross-sectional view schematically showing a nonvolatile protein memory system with optical write/erase and electrical readout capability.

FIG. 1 shows a schematic plane view and a schematic cross-sectional view of a nonvolatile protein memory system with optical write/erase and electrical readout capacity.

The nonvolatile protein memory system includes a memory cell 100, a light source 200, and a readout circuit 300.

The memory cell 100 includes a substrate 10, a microfluidic channel 20, a photosensitive protein 30, and at least a pair of electrodes 40 and 50.

The substrate 10 may include any material as long as it has appropriate properties for forming a microfluidic channel 20. Meanwhile, in order for the nonvolatile protein memory system to be applied to a memory system for writing biological/biochemical information, the substrate 10 may be formed of a biocompatible material. In addition, the memory cell 100 may be formed of a light transmittable material which may transmit light from a light source 200 for writing and erasing data. Thus the substrate 10 may be formed of a COC (cyclic olefin co-polymer), PDMS (polydimethylsiloxane), PMMA (polymethyl methacrylate), PC (polycarbonate), and the like. A surface 10a formed with the electrodes 40 and 50 may be capacitively coupled with the first and second electrodes 40 and 50, so it may be provided at a thickness of less than or equal to several hundred micrometers, and preferably less than or equal to about 100 μm. Thus the surface 10a of the electrodes 40 and 50 may be formed of a biocompatible and transparent plastic such as COC, PDMS, PMMA, PC, and the like.

The photosensitive protein 30 in the microfluidic channel 20 may be positioned in an initial digital state (e.g. a state "0") using isoelectric focusing (IEF).

For the IEF, it may use CA (carrier ampholyte)-IEF or IPG (immobilized pH gradient)-IEF in which a polyacrylamide gel is copolymerized and immobilized with a pH gradient.

In addition, for positioning in an initial digital state, it may further perform focusing to separate a photosensitive protein 30 according to an isoelectric point, and mobilizing the focused protein to a separating region, wherein the mobilization may include chemical mobilization, electro-osmotic flow mobilization, mobilization according to a pressure difference, and the like. Among them, it may be preferable to use a pressure difference mobilization method without using the pump disclosed in Korean Patent Application No. 10-2017-0038364 filed by the present inventors.

Figure 2:
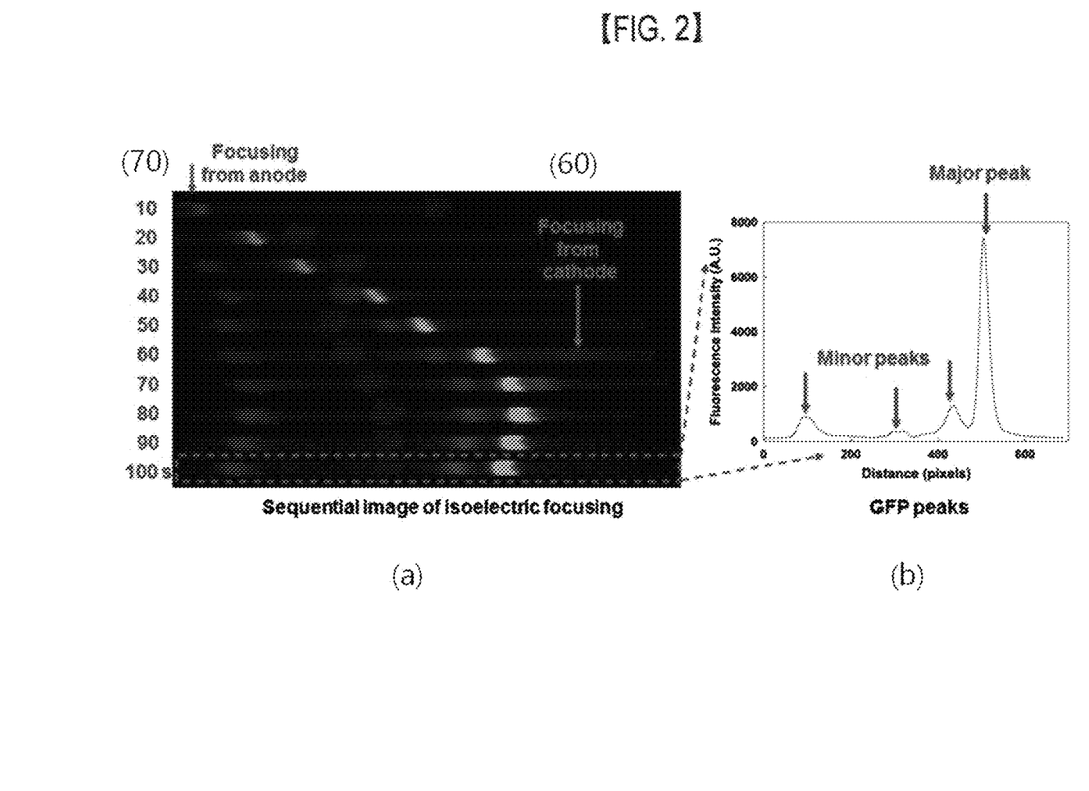
FIG. 2 shows an image of CA-IEF (Carrier Ampholyte IsoElectric Focusing) of GFP (Green Fluorescent Protein) which is a photosensitive protein (a), and a fluorescent intensity measurement graph (b).

FIG. 2 shows an image of a CA-IEF process of GFP (Green Fluorescent Protein) of a photosensitive protein 30 (a), and a fluorescence intensity measurement graph (b).

Referring to FIG. 2, when 10 μM of GFP (Green Fluorescent Protein) is inserted into a straight-line-shaped channel (50 μm×10 μm×10.4 mm), and 70 mM of an anode 60 buffer including an anti-convective medium of 2.5% HEC (hydroxy-ethyl cellulose), a CA (carrier ampholyte) (20 mM) buffer, and a 20 mM cathode 70 buffer are inserted, and a voltage of about 200 V is applied, it is confirmed that GFP is focused about 30-60 times in concentration within about 1-1.5 minutes.

CA-IEF takes less than or equal to about 1 hour, for desirable example, less than or equal to about 30 minutes, or less than or equal to about 10 minutes, for focusing a photosensitive protein, and the chip may be reused.

IPG-IEF may be more effective in improving stability of the protein memory than the CA-IEF. IPG-IEF uses an IPG (immobilized pH gradient) of which the pH gradient is copolymerized in a polyacrylamide gel and immobilized instead of CA, so the pH gradient is stable enough to prevent drifting of the focused protein.

Figure 3:
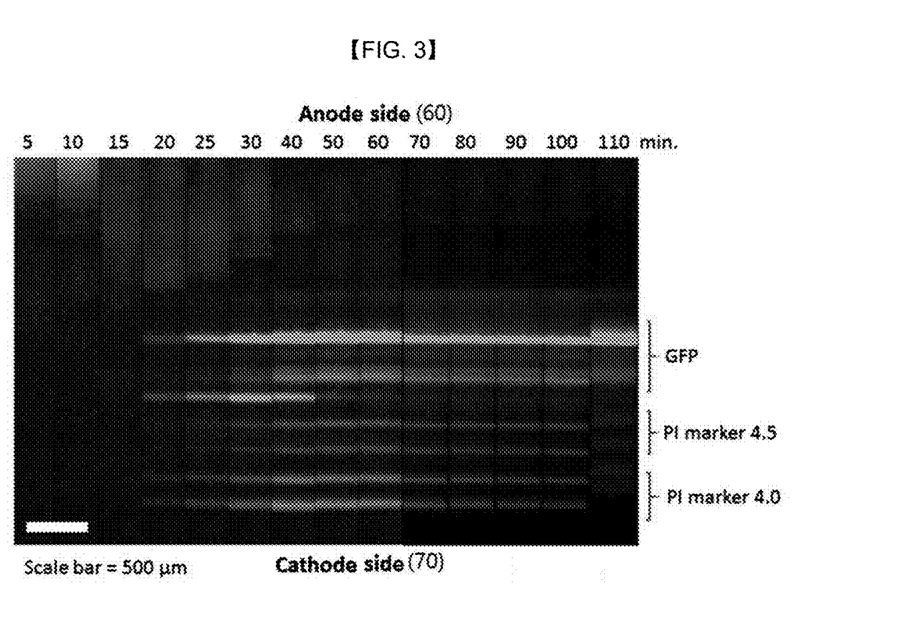
FIG. 3 is an image after conducting IPG (immobilized pH gradient)-IEF.

FIG. 3 is an image after forming IPG (immobilized pH gradient)-IEF. 6% T acrylamide gel is patterned in a membrane shape on one side of the microfluidic chip. Then two solutions with pH 3.8 and 7.0 are prepared by appropriately mixing an acrylamido buffer, an acrylamide monomer, and photoinitiators, and are then injected to respective terminal ends of the microfluidic chip which is then held for 48 hours in a light-blocked space to provide a gradient of pH 3.8-7.0 by diffusion through a microfluidic channel. When irradiating UV overall onto the chip formed with the pH gradient, the acryl amido buffers are copolymerized with a gel to produce an immobilized pH gradient (IPG). The GFP protein is injected to the IPG through electrophoresis, and the GFP is focused onto the corresponding isoelectric point after 20 minutes as shown in FIG. 3. In FIG. 3, PI markers 4.0 and 4.5 are added to determine an isoelectric point of GFP. It is confirmed that the peak becomes sharper as the concentration increasing according to the passage of time, and it is confirmed that the peak drifting does not occur for 90 minutes, unlike the CA-IEF.

The pH gradient is stable when using the IPG-IEF, so the readout operation, focusing on a protein, may be stably performed.

Referring to FIG. 1 again, the photosensitive protein 30 may include any protein as long as it may be photosensitively oxidized and reduced (electron in-out). Representative examples of the photosensitive protein 30 may include a wild-type or genetically modified GFP or RFP (Red Fluorescent Protein), bacteriorhodopsin, cytochrome C, and the like. The genetically modified RFP may include one disclosed in Korean Patent Application No. 10-2017-0024793 filed by the present inventors.

The electrodes 40 and 50 may be formed with any materials as long as they can function as electrodes, but they may be formed with biocompatible electrode materials considering the application to a living body. The biocompatible electrode material may include gold, platinum, ITO, a conductive polymer, carbon, and the like.

The readout circuit 300 may include any circuit as long as may read out information stored in a form of a position change of a photosensitive protein 300 in an optical, electrical, or mass manner. Among them, the electrical method may include a voltage method, a current method, a conductivity method, a non-contact conductivity method, and the like. When applying the non-contact conductivity method, it does not require inserting an electrode into a channel, so the process is simplified, and side effects such as electrolysis may be minimized, so it is considered as a desirable readout circuit. As it uses a high frequency, it may be accomplished in a non-contact manner, and the non-contact conductivity method may be accomplished with coupling electrodes 40 and 50 and an impedance measuring circuit. The impedance measuring circuit is down-sized and easily accomplished since it may be manufactured by a CMOS integrated circuit process.

Examples of the impedance measuring circuit for the readout circuit 300 may include Korean Patent Application No. 10-2015-0067259 invented by the present inventors, i.e., "Analog-digital converter calibration method and analog-digital converter with self-calibration function."

However, the readout circuit 300 may employ various methods of measuring impedance as long as it may realize the non-contact conductivity method.

Figure 4:
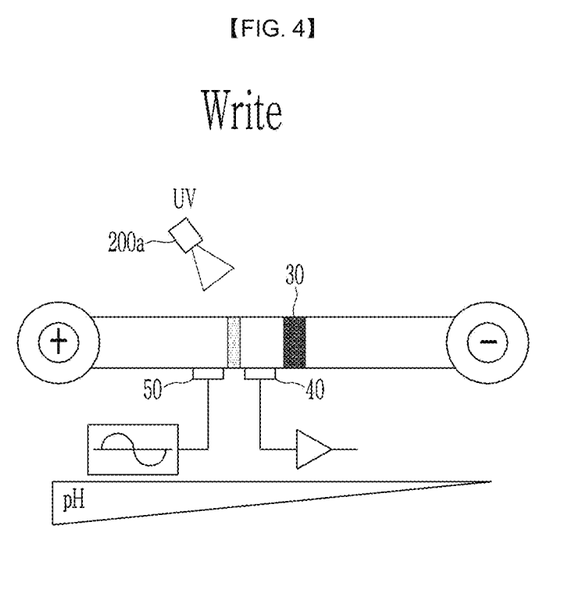
FIG. 4 is a schematic view showing an optical writing operation of a nonvolatile protein memory system according to an embodiment.

FIG. 4 is a schematic view showing an optical write operation of a nonvolatile protein memory system according to an embodiment.

The photosensitive protein 30 may have a first PI (isoelectric point) at the first IEF. This state denotes '0'. Subsequently, when light of a first light source 200a is irradiated to the memory cell 100, the isoelectric point is shifted to a second PI while the electrical state of the photosensitive protein 30 is changed, so the position change occurs.

When the photosensitive protein 30 is GFP, the first PI may correspond to a low pH, and the second PI may correspond to a high pH. The photosensitive protein 30 is disposed outside of the electrodes 40 and 50 at the first PI, and then disposed between the electrodes 40 and 50 at the second PI.

Meanwhile, the shifting of a photosensitive protein 30 may be maximized by providing a pH gradient of the microfluidic channel 20 within a narrower range than about 3-10, for example, a range of about 4-7.

UV is exemplified as the light from the light source 200a, but other wavelength of light may be used depending upon a kind of the used photosensitive protein 30. Particularly, considering the application of being embedded in a living body, it may include a skin transmittable light source.

When the concentration of the photosensitive protein 30 between the electrodes 40 and 50 is increased, the memory cell 100 is changed to the high impedance state. Even after the light source 200a is turned off, the device may continuously maintain the high impedance state.

FIG. 4 shows that only a part of the photosensitive protein 30 is shifted to the second PI. However, by changing the structural or chemical characteristics of the photosensitive protein 30, the conversion rate may be improved, and for example, the conversion rate may reach close to 100%.

Figure 5:
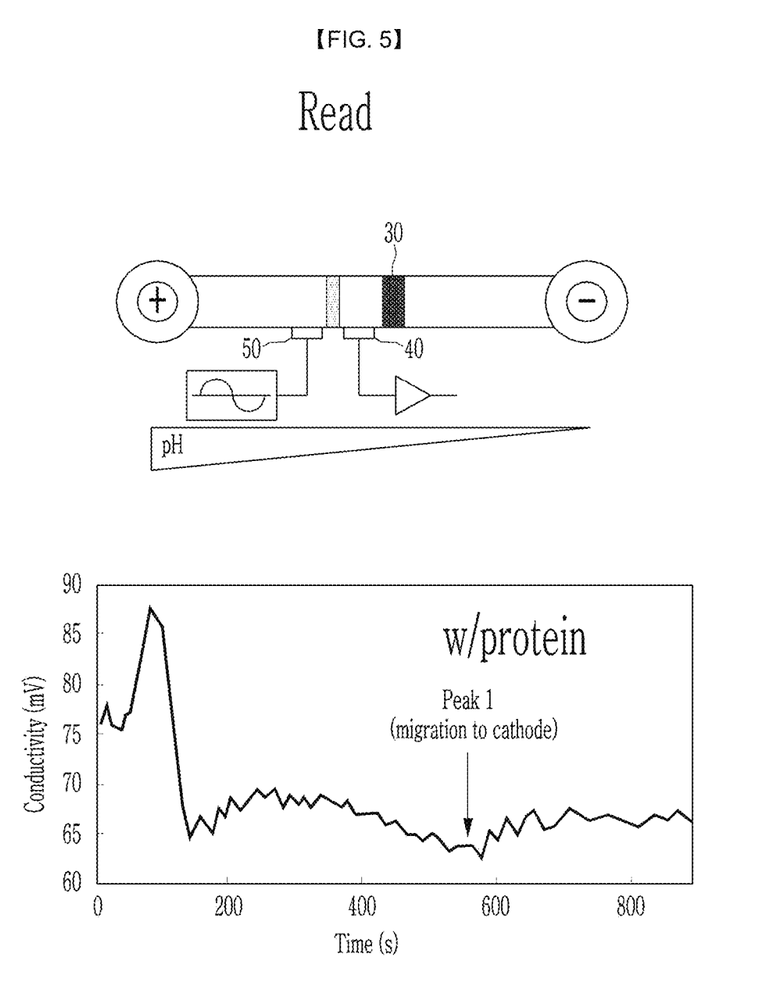
FIG. 5 is a schematic view showing an electrical reading operation of a nonvolatile protein memory system according to an embodiment.

FIG. 5 is a schematic view showing an electric read operation of a nonvolatile protein memory system according to an embodiment.

When the concentration of the photosensitive protein 30 between the electrodes 40 and 50 is increased, the memory cell 100 is changed to a high impedance state. Accordingly, it may read the state of the memory cell by measuring the impedance between the electrodes 40 and 50. If the first PI state is set as '0', the state that the photosensitive protein 30 is between the electrodes 40 and 50 at the second PI state may be estimated as '1.'

In FIG. 5, when the photosensitive protein 30 is disposed between the electrodes 40 and 50, it shows one example of detecting it as a reversed peak. The reversed peak shows an inverse of the impedance. In other words, FIG. 5 shows an exemplary detecting method showing that the electrical conductivity is locally reduced according to the characteristics of the isoelectric focusing.

Figure 6:
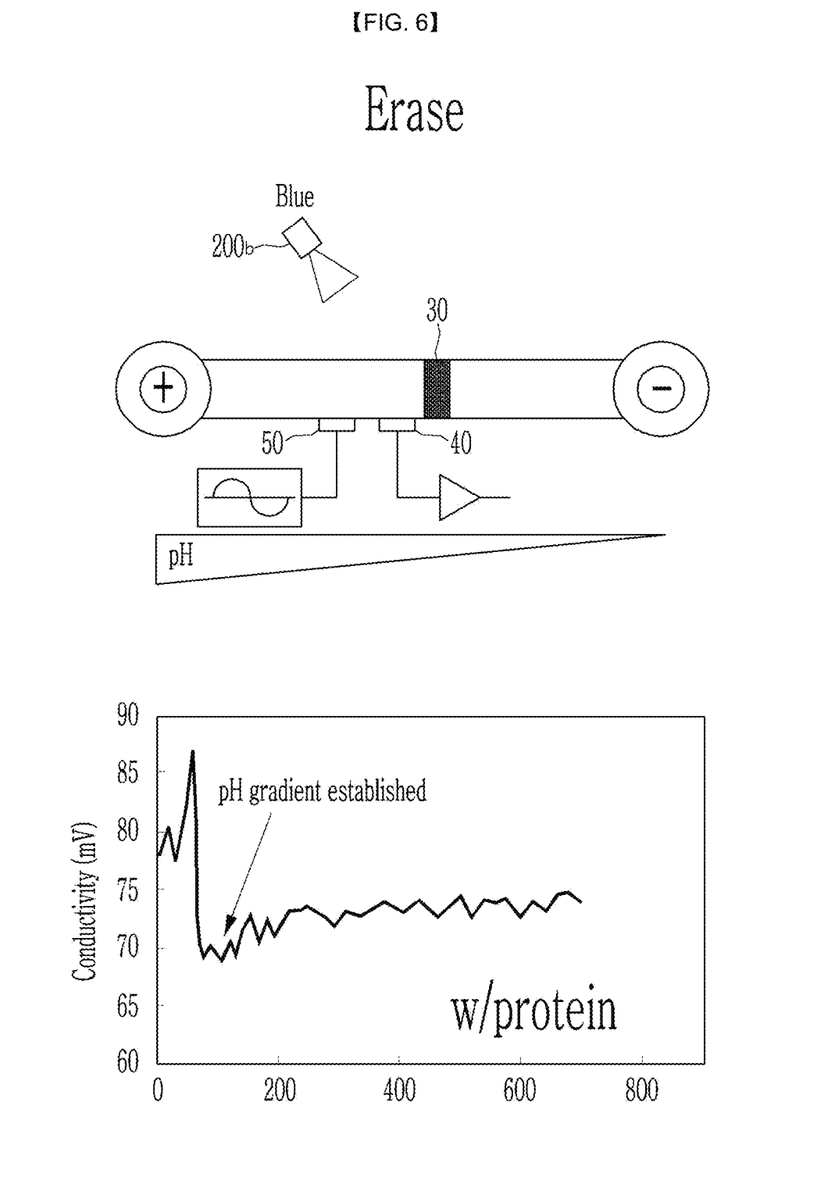
FIG. 6 is a schematic view showing an optical erasing operation of a nonvolatile protein memory system according to an embodiment.

FIG. 6 is a schematic view showing an optical erase operation of a nonvolatile protein memory system according to an embodiment.

When a second light source 200b is irradiated to the photosensitive protein 30 of the memory cell 100, the reverse reaction occurs to return the photosensitive protein 30 to the low PI again. As a result, it converts to the low impedance state. Accordingly, it is understood that the reversed peak disappears, unlike in the conductivity graph shown in FIG. 5. When UV is employed as the light of the first light source 200a, the second light source 200b may employ blue light. Even after the second light source 200b is turned off, the memory cell 100 may continuously maintain the low impedance state.

For the first light source 200a and the second light source 200b, a green light-red light combination or a UV-green light combination may be employed, besides the UV-blue light combination. The first light source 200a and the second light source 200b may use an element having light of a certain wavelength such as an LED or an optical filter combined with a white light source.

Figure 7:
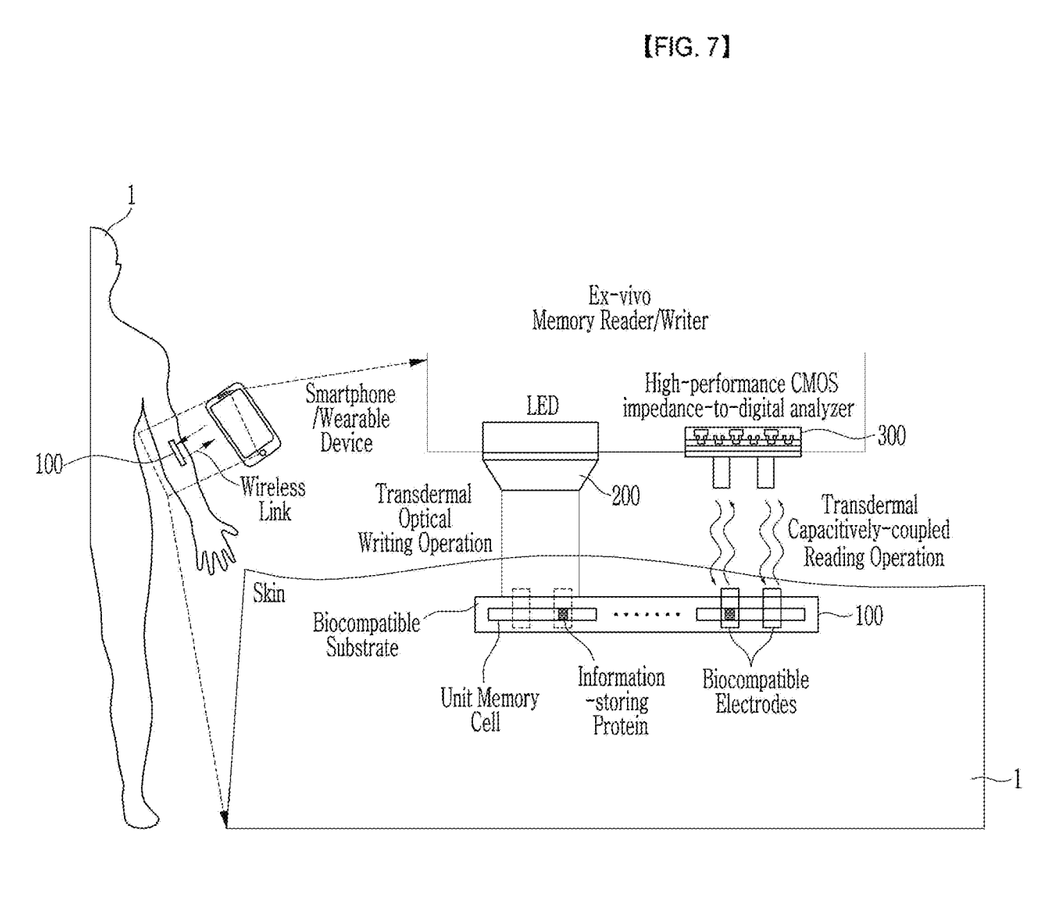
FIG. 7 is a schematic view showing a case that a nonvolatile protein memory system according to an embodiment is employed for a living body.

The nonvolatile protein memory system according to an embodiment may have high biocompatibility and may measure the read operation by non-contact conductivity measurement. Accordingly, as shown in FIG. 7, the memory cell 100 may be embedded in vivo, and a light source 200 and a readout circuit 300 may be mounted in vitro, so as to provide a biometric embedded ID card or a biometric embedded credit card or the like.

While this invention has been described in connection with what is presently considered to be practical example embodiments, it is to be understood that the invention is not limited to the disclosed embodiments, but, on the contrary, is intended to cover various modifications and equivalent arrangements included within the spirit and scope of the appended claims.

What is claimed is:

1. A nonvolatile protein memory system comprising at least one memory cell, wherein the memory cell comprises:
   a substrate including a microfluidic channel having a pH gradient;
   a photosensitive protein disposed in the microfluidic channel; and
   a first electrode and a second electrode disposed on the microfluidic channel, spaced apart from each other, and detecting a position change of the photosensitive protein in the microfluidic channel.

2. The nonvolatile protein memory system of claim 1, wherein the photosensitive protein in the microfluidic channel is disposed in an initial digital state by isoelectric focusing.

3. The nonvolatile protein memory system of claim 2, wherein the isoelectric focusing is carrier ampholyte isoelectric focusing or immobilized pH gradient isoelectric focusing.

4. The nonvolatile protein memory system of claim 1, wherein the photosensitive protein is a wild-type GFP, a wild-type RFP, a genetically modified GFP, a genetically modified RFP, a wild-type bacteriorhodopsin, a genetically modified bacteriorhodopsin, a wild-type cytochrome C, or a genetically modified cytochrome C.

5. The nonvolatile protein memory system of claim 1, wherein the memory cell performs write and erase by a position change of the photosensitive protein in the microfluidic channel.

6. The nonvolatile protein memory system of claim 5, wherein the write and erase are performed by a pair of light sources having different wavelengths from each other.

7. The nonvolatile protein memory system of claim 6, wherein the pair of light sources comprise a UV-blue light combination, a green light-red light combination, or a UV-green light combination.

8. The nonvolatile protein memory system of claim 1, wherein the substrate comprises a light transmittable biocompatible plastic material.

9. The nonvolatile protein memory system of claim 1, wherein the information stored by the position change of the photosensitive protein is read out in an electrical manner.

10. The nonvolatile protein memory system of claim 9, wherein the electrical readout is performed using a non-contact readout circuit.

11. The nonvolatile protein memory system of claim 9, wherein the non-contact readout circuit is a readout circuit measuring impedance between the first and second electrodes in a non-contact manner.

12. The nonvolatile protein memory system of claim 1, wherein the pH gradient is about 3-10.

13. The nonvolatile protein memory system of claim 1, wherein the substrate, the first electrode, and the second electrode comprise a biocompatible material.

14. A nonvolatile protein memory system comprising:
a memory cell including a substrate including a microfluidic channel having a pH gradient, a photosensitive protein disposed in the microfluidic channel, and a first electrode and a second electrode disposed on the microfluidic channel and spaced apart from each other and detecting a position change of the photosensitive protein in the microfluidic channel;
a light source causing a position change of the photosensitive protein; and
a readout circuit measuring impedance between the first electrode and the second electrode in a non-contact manner.

15. The nonvolatile protein memory system of claim 14, wherein the photosensitive protein is positioned at the initial digital state by carrier ampholyte isoelectric focusing or immobilized pH gradient isoelectric focusing.

16. The nonvolatile protein memory system of claim 14, wherein the light source comprises a UV-blue light combination, a green light-red light combination, or a UV-green light combination.

17. The nonvolatile protein memory system of claim 14, wherein the memory cell is embedded in vivo, and the light source and the readout circuit are mounted in vitro.

18. The nonvolatile protein memory system of claim 16, wherein the memory cell is a biometric embedded ID card or biometric embedded credit card.

* * * * *